United States Patent [19]

Lloyd

[11] Patent Number: 5,846,903
[45] Date of Patent: Dec. 8, 1998

[54] WATER DISPERSIBLE GRANULES OF LOW MELTING POINT PESTICIDES

[75] Inventor: John M. Lloyd, Richmond, New Zealand

[73] Assignee: ICI Australia Operations Proprietary Ltd., Melbourne, Australia

[21] Appl. No.: 6,303

[22] Filed: Jan. 22, 1993

[30] Foreign Application Priority Data

Jan. 24, 1992 [NZ] New Zealand .............................. 241388

[51] Int. Cl.⁶ ...................................... A01N 25/14

[52] U.S. Cl. ........................ 504/116; 424/408; 514/949; 514/952

[58] Field of Search ........................ 504/116; 71/DIG. 1; 424/408; 514/949, 952

[56] References Cited

U.S. PATENT DOCUMENTS

| | | | |
|---|---|---|---|
| 4,348,385 | 9/1982 | Synek | 514/970 |
| 4,979,979 | 12/1990 | McCollum, III et al. | 71/DIG. 1 |

FOREIGN PATENT DOCUMENTS

| | | |
|---|---|---|
| B-5700/90 | 2/1991 | Australia . |
| 112438 | 7/1984 | European Pat. Off. . |
| 447056 | 9/1991 | European Pat. Off. . |
| 2245494 | 1/1992 | United Kingdom . |

*Primary Examiner*—S. Mark Clardy
*Attorney, Agent, or Firm*—Pillsbury Madsion & Sutro LLP

[57] ABSTRACT

Water dispersible granules are prepared that contain low melting point pesticides and which are prepared by milling the pesticides with a first portion of finely divided filler and blending the milled mixture with a second portion of finely divided filler, wetting the blend with water and then forming granules from the wetted blend.

8 Claims, No Drawings

WATER DISPERSIBLE GRANULES OF LOW MELTING POINT PESTICIDES

TECHNICAL FIELD OF INVENTION

This invention relates to water dispersible granules for the delivery of biologically active substances for agricultural use. More particularly it relates to granules comprising biologically active substances that have low melting points.

BACKGROUND OF THE INVENTION

Water dispersible granules (WG), also known as dry flowables, have recently become a widely accepted form for a range of biologically active agents, and in particular for pesticides.

Water dispersible granules consist of small granules typically 0.1 to 3 mm in size and preferably of uniform size range and which are free flowing, low dusting and disperse in water to form a homnogenous suspension of particles that are substantially smaller than that of the granules. The granules can be measured volumetrically which enables the end user to conveniently measure the desired amount of product for addition to a spray tank.

Typically, water dispersible granules comprise an active agent, a filler (also referred to as diluent) and surface active agents (which term may include a dispersant and a wetting agent). The relative amounts of individual ingredients may vary widely, with the active agent generally being present in an amount from 10 to 95% w/w, the filler in an amount from 5 to 80% w/w and the surface active agent in an amount from 0.1 to 20% w/w.

The conventional process for preparing water dispersible granules consists of a preliminary step of forming a wettable powder by blending the ingredients, active agents, filler and surface active agent, and milling them to provide the desired particle size. The wettable powder is then subsequently formed into granules by a range of techniques including agglomeration and extrusion or spray drying in each case after the addition of water and optionally binding agents.

Examples of such processes are described by D A Hovde in the paper entitled "Laboratory Development and Evaluation of Water Dispersible Granules" presented at: ASTM E-35.22 Symposium on Pesticide Formulations and Application Systems: Third Symposium, Oct. 11–14 1992, Fort Mitchell, Ky.

while such processes are generally acceptable, it is not always possible to achieve good dispersibility with all formulations especially with compositions where the active agent is a low melting point solid of low water solubility. In such cases we have found that, while the intermediate wettable powder may disperse adequately, the resulting granule does not.

U.S. Pat. No. 4,511,395 of Misselbrook discloses a method of preparing WG with the dinitroaniline class of herbicides. His process relies on the use of naturally occurring swelling hydrous aluminium silicate clay. After preparing and drying the granules, 0.25–1.0% of fumed hydrophobic silica is added to the granules to aid their free flowing characteristics. Whilst this invention appears to give favourable results its applications seems to be restricted to the dinitroaniline class of herbicides. Also, it appears sufficient with this class of active material for the additional filler to be added after the granules are prepared.

It is an object of the present invention to provide water dispersible granules containing low melting point active agents that have improved dispersibility.

SUMMARY OF THE INVENTION

Accordingly in one aspect this invention provides a process for producing a water dispersible granule comprising milling a biologically active substance that has a low melting point with a first portion of a finely divided filler to give a finely divided mixture, and then blending a second portion of filler along with a surfactant component with the finely divided mixture, wetting the blend with water and then granulating the blend.

Preferably the first and second portions of the filler component comprises 25 to 90% w/w of the granule.

Preferably the finely divided mixture after the milling stage has a particle size less than 50 microns.

Preferably the biologically active substance has a melting point less than 100° C. and a water solubility less than 100 mg/litre at 25° C.

In an alternative aspect this invention provide a process for preparing water dispersible granules containing between 5–75% w/w of a biologically active substance, 25–90% w/w of a filler component and 5–15% of a surfactant component, the process comprising milling the active ingredient component in admixture with 20–80% the filler component, subsequently adding the balance of the filler along with the surfactant component; blending and wetting the composition with water and then granulating this mixture.

It is preferred that the surfactant component is added after the milling stage but acceptable results can be achieved with all or part of the surfactant component being added during or prior to the milling stage.

DETAILED DESCRIPTION OF THE INVENTION

The process in accordance with the invention comprises effectively three stages, A first stage in which the active ingredient is generally blended with a portion of the filler. This blending stage is contrasted with the milling stage. In milling, the ingredients are subject to high energy mixing such as by an airmill or a hammer or pin disc mill. It is this high energy milling, which gives very intimate mixing of the active ingredient and the filler which is believed ensures active ingredient is distributed uniformly throughout the final granule. However it is also believed, without being bound by any theory, or limiting the scope of the invention, that the high energy input of milling causes the low melting point solid active ingredient to flow and form a coating over the first portion of filler particles. In the third stage where the additional filler is added, along with the surfactant and other components if desired, the blending process is much less energy intensive, than the milling stage, the "precoated" filler particles are separated from each other by uncoated filler particles which enables each of the particles to segregate readily from each other on dispersion in water. It is believed that where the filler and active ingredient are milled together, subsequent granulation causes the "coated" filler particles to adhere together which makes it difficult for the individual particles to disperse. Similarly, if the third stage blending is a high energy milling process similar unfavourable results are achieved.

The improvement using the process of the present invention is most notable in instances where the active ingredient comprises one or more active substances having a melting point of less than 100° C. and a water solubility of less than 100 mg/litre. Examples of such substances include the following (melting point in ° C. and water solubilities at ambient temperature shown in parenthesis):

Aldrin (49–60; <<1 mg/l)
Azinphocs ethyl (73–74; 33 mg/l)
Benfluralin (65–66.5; <1 mg/l)
Bensultap (82–83; 0.7 mg/l)
Benzoxisate (73; 30 mg/l)
Bifenthrin (51–66; 0.1 g/l)
Binapacryl (66–67; insoluble)
Bromphos (53–54; 40 mg/l)
Bromopropylate (77; <5 g/l
Butralin (60–61; 1 mg/l)
Chlorphoxim (66.5; 2 mg/l)
Chlorpyrifos (42–43.5; 2 mg/l)
Pluchloralin (42–43.5; <1 mg/l)
Fluroxypyr (56–57; 0.9 mg/l)
Nitrothal-isopropyl (65; 0.39 mg/l)
Phosmet (72.5; 25 mg/l), Pirimicar (90.5:2.7 g/l)
Tefluthrin (44.6;0.02 mg/l) Napropamide (75; 73 mg/l)

Minor amounts of active substances that are not low melting point solids may be used but in such cases the active substance will preferably comprise at least 90% by weight of compound or compounds having a melting point less than 100° C. and a water solubility of less than 100 mg/litre.

One particular active agent in which water dispersibility is improved by the process of the invention is azinphosmethyl. In accordance with one preferred embodiment of the invention a process for preparation of a water dispersible granule containing in the range of from 25 to 50% w/w of azinphosmethyl, comprises: milling a composition comprising between 40–80% w/w azinphosmethyl and between 20–60% w/w filler, adding additional filler equivalent to between 22.5 and 58.75% w/w of the final product along with surfactants equivalent to 10–15% w/w of the final product, blending and wetting the composition then granulating same.

The quantity of active ingredient in the milled premix may vary from about 25% to 100% depending on the physical characteristics of the active ingredient, the desired content of the same in the final granule and the particle size of the premix. The milling step is the more expensive step in the whole procedure and therefore it is desirable to minimise costs involved at that state. This will however, involve balancing competing factors. A reduction in the amount of filler will reduce the milling time down to a certain concentration of filler, but on the other hand milling a higher concentration of active ingredient will prove more difficult as that concentration increases. moreover, the high concentration of active ingredient may require more elaborate milling conditions such as reducing the temperature of the milling chamber substantially by introducing special cooling facilities.

It is generally preferable for the concentration of active ingredient in the premix to be at least 1.5 times that desired in the final granule. Thus for example a 50% azinphosmethyl granule would be preferably prepared from a premix containing at least 75% active ingredient w/w. Where a 35% azinphos-methyl granule is desired, the premix should contain slightly more than 50% active ingredient.

Milling very high concentration of an active ingredient, such as in the extreme where very little filler is present, does become technically very difficult. In all milling operations involving low melting point solids, it is necessary to avoid raising the temperature of the active ingredient above its melting point and preferably the milling temperature should be kept low enough to prevent the active from becoming too soft and hence flowing too freely or making it very difficult to reduce to discrete particles. To maintain these optimum conditions, chilled air is desirably fed into the milling chamber, while in cases where the ratio of active substance to filler is high, the use of chilling conditions will be essential. If it is desired to attempt to mill a high concentration of active ingredient with little filler present, it will still generally be necessary to use a grinding aid such as precipitated silica, usually at the rate of 10% or more of the weight of the premix. Whilst the general temperatures of milling should be maintained at less than the melting point of the microscopic level such as the particle surface, localised temperatures may exceed the melting point of the active substance and indeed it is believed this is an important mechanism for better results.

The maximum particle size of the active ingredient that can be milled in accordance with the invention does depend on the type and size of the particular mill. With large airmills, particle sizes up to 5 mm in diameter may be introduced while smaller mills may require the particle size to be reduced to less than 0.5 mm before milling takes place.

It is also generally desirable to select the particle size of the filler consistent with that of the active ingredient prior to milling. If the filler is initially in a very finely divided state, separation of that fine filler from the active ingredient may occur in the mill chamber. It is therefore preferable to use a relatively coarse filler, for example, having an upper particle size of 150 microns or more. The optimum particle size for a particular filler and active ingredient can be determined by experimentation on the particular mill that is to be used. Generally, in accordance with the invention, the filler materials are less than 150 microns. The particle size of the milled premix is generally such that less than 1%, more preferably less than 0.5%, is retained on a 53 micron aperture sieve. The range of particles sizes below 53 microns is generally such that greater than 80% is less than 10 micron.

It is desirable in accordance with the invention for the milled premix to be blended with the additional filler and other additives as desired, shortly after the milling step. There is a tendency for the finely divided premix to cake up if stored for too long. In accordance with the invention, the blending of the additional filler and other additives as desired, with the premix, can take place initially and the blended formulation can then be stored. Granulation can then take place at a time and place most convenient for that particular formulation and to suit the particular end use.

The additional filler that is blended with the milled premix prior to granulation will vary depending on the physical characteristics of the active and on the particle size of the premix. In the case of very soft waxy active ingredients, it is generally desirable to use a filler that has been ground to a very fine particle size, i.e. generally less than 10 microns. This provides a greater surface area which is believed to yield better separation of the "precoated" premix particles when the mixture is granulated. Where the active ingredient is not as soft, the filler can be coarser. The benefit of a larger particle is in enabling a reduction in the amount of surfactant required in the formulated product because of the reduced surface area of the filler. While there will be a degree of experimentation in each particular case to assess the optimum particle sizes of the additional filler to the premix, in general terms, the additional filler should not exceed the particle size of the premix.

The additional filler and surfactants and other components are blended with the premix then following the blending operation, water is added and granulation takes place in the normal manner.

Blending can take place using normal equipment, e.g. a ribbon blender. Surfactants can be blended at this stage or added along with the water used during the granulation process. When granulating, water is added and after granulation, the granules are dried.

The milling equipment used in the process of the invention may be any suitable type of milling equipment known in the art. Examples include fluid energy mills using air or inert gas and mechanical mills such as hammer or pin disc mills. Where the active ingredient used in the process of the invention is a solid of waxy consistency having a melting point of less than 100° C. it is preferred to use a fluid energy mill as waxy compounds have a tendency to build up on the moving parts of mechanical mills, The term surfactant is herein used in the broad sense to include materials which may be referred to as emulsifying agents, dispersing agents and wetting agents and the surfactant component may comprise one or more surface active agents selected from the anionic, cationic and nonionic type.

Examples of surfactants of the anionic type includes soaps, salts of aliphitic monoesters or sulphuric acid such as sodium lauryl sulphate, salts of sulphonated aromatic compounds, for example sodium dodecylbenzenesulphonate, sodium, calcium or ammonium lignosulfonate or butylnaphthalene sulphonate, and a mixture of the sodium salts of diisopropyl- and triisopropyl-napthalene sulphonates. Suitable agents of the non-ionic type include, for example, the condensation products of ethylene oxide with fatty alcohols such as oleyl alcohol or cetyl alcohol, or with alkyl phenols such as octyl phenol, nonly phenol and octyl cresol. Other nonionic agents are the partial esters with ethylene oxide and the lecithins and phosphoxylated surfactants such as phosphorylated ethylene oxide/propylene oxide block copolymer and ethyloxylated and phorphorylated stryryl substituted phenol.

Preferably the surfactant component will comprise at least one wetting agent such as those selected from alkyl naphthalene sulfonates, phosphate esters, sulphosuccinates and nonionics such as tridexyl alcohol ethoxylate; and/or at least one dispersing agent such as those selected from the group of napthalene condensates, lignosultonates, polycrylates and phosphate esters. Typically the total surfactant component will comprise from 0.1 to 25% and more preferably from 10 to 15% by weight of the dry weight of the granule composition.

The fillers for use in accordance with this invention will be those normally used in granule compositions. Without limiting the type of fillers that can be used, suitable fillers include mineral earths and clays, e.g. kaolin, bentonite, Fuller's earth, attapulgite diatomaceous earth, talc, dolomite and other inorganic, generally inert, substances as well as organic materials, e.g. synthetic polymers, e.g. ground or powdered plastics and resins. Generally the filler component will have a bulk density (vibrated) in the range of from 200 to 650 g/l. Particularly preferred fillers include talc, mica and fused sodium, potassium, aluminium silicates. Mixtures of different fillers may be used and the composition and/or characteristics of the first portion of tiller may differ from the second portion of filler.

The method by which the granules are formed in accordance with the invention is not narrowly critical and a range of granulation techniques are known in the art. However, we have found the granulation technique described in our copending application PCT/AU 88/00201 to be particularly advantageous. In that application a low pressure wet mix extrusion process is used, followed by gentle rolling or tumbling to reduce the size and round the granules. A drying step is then usually incorporated.

The invention will be further described by reference to preferred embodiments illustrated in the following Examples:

EXAMPLE 1

Preparation of water dispersible granules with 25% active ingredient using the process of the invention.

A sample of water dispersible granules comprising 25% a.i. w/w Fenoxydim herbicide Z-[1-(ethoxyimino)propyl]-3-hydroxy-5-(3-butyryl-2, 4, 6-trimathylphenyl)cyclohex-2-en-1-one a member of the cyclohexone-dione herbicides disclosed in Australian Patents 464555, 555884, 556148 and 566671 was prepared from a high strength airmilled premix comprising 50% a.i. w/w Fenoxydim.

Premix Formula Example 1

| Ingredient | % w/w |
| --- | --- |
| Technical Grade Fenoxydim | 51.03 |
| Mica 20 (20 micron, ex Mintech NZ Ltd) | 48.97 |

Premix Preparation

Technical grade Fenoxydim was first pulverised to a particle size predominantly less than 250 μm prior to blending with the other ingredient. The blended premix was then finely ground in a 200 mm dia. airmill for two minutes under an air pressure of 620 kpa.

Preparation of Water Dispersible Granules

The 50% a.i. w/w/Fenoxydim airmilled premix was first diluted by blending with the additional ingredients in the proportion shown below. The dry mixture was then blended with water and granulated according to the procedure described PCT Patent Application 88/00201, Example 1 where a wet premix is extruded under relatively low pressure of approximately 20 psi by a reciprocating extruder, gently rolling the low compact extrudate to give granules 2 to 3 times their diameter.

Diluted Mixture

| | % w/w |
| --- | --- |
| 50% a.i. w/w Fenoxydim airmilled premix | 50 |
| Morwet D425 | 10 |
| Mica 20 | 39.5 |
| Residual Water | 0.5 |

Laboratory Tests

Samples were tested initially and after 12 weeks storage at a constant 50° C.

Wet sieve analysis of an aqueous suspension of granules was determined after a 50 g sample of granules is dispersed with gentle agitation for five minutes in water (250 ml) in a beaker, The suspension was gently rinsed through the sieve using only a gentle stream of water.

|  | % retained on 53 μm aperture test sieve | |
| --- | --- | --- |
|  | Initial | 12 Weeks |
| EXAMPLE 1 | 0.013 | 0.210 |

The suspensibility was determined by dispersing with gentle agitation a 7.5 g sample of granules in 250 ml of water in a stoppered 250 ml measuring cylinder and allowing settlement to take place for 30 minutes at 30° C. After this period of time 90% of the suspension is removed and the solids of the remaining 10% of the suspension determined to allow calculation of the percent suspended in the top 90%. The results of this test showed that initially 69% was suspended and that after twelve weeks storage 68%, or almost the same amount was suspended and the sieve residue was well within specification of 0.5% maximum.

EXAMPLE 2

Comparative example of a water dispersible granule comprising 25% a.i. w/w Fenoxydim prepared with all the components milled together.

The mixture was prepared by processing Premix Formula Example 2 by the process of Example 1 and converted to granules also by the method of Example 1.

Premix Formula Example 2

| Ingredient | % w/w |
| --- | --- |
| Technical Grade Fenoxydim | 25.52 |
| Morwet D425 | 10.00 |
| Mica 20 | 63.98 |
| Residual Water | 0.50 |

Laboratory tests on these granules were performed as in Example 1 and these showed that whilst initially only 0.012% residue remained after wet sieve analysis after twelve weeks storage at 1.125% residue was found which is well outside of the usual specification of 0.5% max and shows the sample deteriorated on accelerated storage. This was much worse than the result for Example 1 according to the invention.

The suspensibility, whilst initially good at 74%, had deteriorated after twelve weeks to 62% which is a significantly worse result than for Example 1.

EXAMPLE 3

This example illustrates the preparation of 50% a.i. azinphos-methyl WG prepared from an airmilled 75% a.i. premix.

High Strength Premix (75% a.i. Azinphos-methyl)

|  | % w/w |
| --- | --- |
| Azinphos-methyl technical (95.9% a.i.) | 78.21 |
| Talc Ultrafine 5 | 21.79 |
|  | 100.00 |

Formula No. 3 Water Dispersible Granules

|  | % w/w |
| --- | --- |
| a.i.airmilled azinphos-methyl 75% premix | 67.67 |
| Morwet D425 | 9.00 |
| Sellogen HR | 3.00 |
| 'Talc Ultrafine 5' | 21.33 |
|  | 100.00 |

The azinphos-methyl technical was prepared by mechanically crushing through a 0.85 mm aperture screen and the high strength premix was hand blended in a sealed polythene bag.

The blended premix was milled in a 200 mm diameter airmill fitted with an inline water cooled heat exchanger. The milling air pressure was 660 kPa.

The milled product was then granulated according to the process described in Example 1 of PCT/AU/88/00201 via a laboratory granulator. The wet granules were dried in a static bed dryer at an air temperature not exceeding 35 deg. C.

Samples of dried granules were screened 450–1180 μm and tested in the laboratory initially and after periods of storage at a constant 50 deg. C.

Results are set out below in Table 1.

TABLE 1

| Storage Time at | SIEVE RESIDUES (% Retained, cumulative) | | Dispersion Time | Suspensibility |
| --- | --- | --- | --- | --- |
| 50° C. | 150 μm | 53 μm | (Seconds) | % |
| Initial | 0.01 | 0.15 | 55 | 90 |
| 1 day | 0.88 | 2.09 | 60 | 52 |
| 7 days | 1.06 | 6 | 60 | 48 |

EXAMPLE 4

This example show the preparation of 25% a.i. azinphos-methyl prepared from an airmilled 75% a.i. premix. The granules were prepared and tested as for Example 3 and the results are set out in Table 2.

Formula No. 4

|  | % w/w |
|---|---|
| 75% a.i. airmilled azinphos-methyl premix (see Example 3) | 33.34 |
| Morwet D425 | 9.00 |
| Sellogen HR | 3.00 |
| 'Talc Ultrafine 5' | 54.66 |
|  | 100.00 |

TABLE 2

| Storage Time at 50° C. | SIEVE RESIDUES (% Retained, cumulative) | | Dispersion Time (Seconds) | Suspensibility % |
|---|---|---|---|---|
|  | 150 μm | 53 μm |  |  |
| Initial | 0.01 | 0.02 | 55 | 82 |
| 1 day | 0.02 | 0.40 | 55 | 63 |
| 7 days | 0.01 | 1.06 | 60 | 43 |

EXAMPLE 5

This is a comparative example in which 50% a.i. azinphos-methyl WG is prepared by airmilling a blend of all the ingredients in the formulation. The granules were prepared and tested as for Example 3 and the results are set out in Table 3. These results are inferior to those of Examples 3.

Formula No. 5

|  | % w/w |
|---|---|
| Azinphos-methyl Technical (95.9% a.i.) | 52.14 |
| Morwet D425 | 9.00 |
| Sellogen HR | 3.00 |
| 'Talc Ultrafine 5' | 35.86 |
|  | 100.00 |

TABLE 3

| Storage Time at 50° C. | SIEVE RESIDUES (% Retained, cumulative) | | Dispersion Time (Seconds) | Suspensibility % |
|---|---|---|---|---|
|  | 150 μm | 53 μm |  |  |
| Initial | 2.83 | 13.2 | 60 | 57 |
| 1 day | 31.2 | 52.9 | — | 28 |
| 7 days | 33.6 | 51.6 | — | 26 |

EXAMPLE 6

This is a comparative example in which 25% a.i. azinphos-methyl WG prepared by airmilling a blend of all the ingredients in the formulation.

Formula No. 6

|  | % w/w |
|---|---|
| Azinphos-methyl Technical (95.9% a.i.) | 26.07 |
| Morwet D425 | 9.00 |
| Sellogen HR | 3.00 |
| 'Talc Ultrafine 5' | 61.93 |
|  | 100.00 |

The granules were prepared and tested as in Example 3 to give the results set out in Table 4 which can be seen to be clearly inferior in sieve residues and suspensibility to those of Example 4.

Formula No. 5

|  | % w/w |
|---|---|
| Azinphos-methyl Technical (95.9% a.i.) | 52.14 |
| Morwet D425 | 9.00 |
| Sellogen HR | 3.00 |
| 'Talc Ultrafine 5' | 35.86 |
|  | 100.00 |

The granules were prepared and tested as in Example 3 to give the results set out in Table 3 which can be seen to be clearly inferior to those of Example 3.

TABLE 3

| Storage Time at 50° C. | SIEVE RESIDUES (% Retained, cumulative) | | Dispersion Time (Seconds) | Suspensibility % |
|---|---|---|---|---|
|  | 150 μm | 53 μm |  |  |
| Initial | 0.01 | 0.10 | 60 | 61 |
| 1 day | 0.35 | 5.98 | 70 | 40 |
| 7 days | 0.66 | 12.92 | 80 | 32 |

EXAMPLE 7

This Example, in two parts A and B, illustrates the benefits of having approximately 1.6 times the % level of the active substance in the the milled premix (part B) as compared to the final granule. In part A the concentration to the active substance in the premix is only 1.2 time the % level of active substance in the final granule. In this Example, Devrinol, a post emergent selective broad leaf herbicide is used as the active substance.

EXAMPLE 7A

A low strength premix was prepared and airmilled as follows:

Premix Composition

|  | % w/w |
|---|---|
| Napropamide technical grade, (94.7% a.i.w/w) | 60 |
| Talc 'Superfine 15' | 40 |

The technical grade napropamide was ground and screened −500 μm prior to blending with the talc. The premix was then airmilled at 655–690 kpa.

Preparation

A sample of Devrinol 50% WG was prepared from the following materials in accordance with the procedure described in PCT/AU/88/0620) by using 28 litres of water per 100 kg of dry mix.

| Ingredient | % w/w |
|---|---|
| 60% w/w napropamide premix | 88.0 |
| Morwet D425 | 8.0 |
| Morwet EFW | 2.0 |
| Talc 'Superfine 15' | 2.0 |

The test results are set out below and these show poor storage stability.

| | Wet Sieve Analysis of an aqueous suspension % retained cumulative) | | Time to Disperse |
|---|---|---|---|
| | 150 μm | 53 μm | (Seconds) |
| Initial | 0.35 | 0.49 | 45 |
| After 107 days @ 50 deg C. | Failed to disperse | | |

EXAMPLE 7B

The formulation of Devrinol 50% WG from a higher strength premix was investigated.

Premix Composition

| | % w/w |
|---|---|
| Napropamide technical grade, (94.7% a.i.w/w) | 80 |
| Talc 'Superfine 15' | 20 |

The technical grade napropamide was reduced to a particle size of less than 500μm, blended with the talc and airmilled as described in Experiment A.

Water Dispersible Granule Preparation

A sample of Devrinol 50% was prepared with the following material, using 27.51 of water per 100k of dry mix.

| Ingredient | % w/w |
|---|---|
| 80% w/w napropamide premix | 66.0 |
| Morwet D425 ex De Soto Inc (USA) (Sodium Napthalene Formaldehyde Condensate) | 8.0 |
| Morwet EFW ex De Soto Inc (USA) (Sodium salt of sulfated Alkyl Carboxylate and Alkyl Naphthalene Sulfonate) | 2.0 |
| Talc 'Ultrafine 5' | 23.5 |
| Residual Water | 0.5 |

NOTE: Talc 'Ultrafine 5', a finer version of 'Superfine 15' was used to provide greater separation of the premix particles through increased surface area.

The test results set out below show significantly improved storage stability.

| | Wet Sieve Analysis of of an aqueous suspen. % retained, cumulative | | Time to Disperse | Suspens. (% total |
|---|---|---|---|---|
| | 150 μm | 53 μm | (Seconds) | solids) |
| Initial | 0.003 | 0.22 | 90 | 93 |
| After 91 days @ 50 deg C. | 0.006 | 0.067 | 80 | 80 |

While the invention has been described by reference to preferred embodiments, it is not to be construed as being limited thereto. Moreover, where specific processing steps and materials and apparatus have been described, and known equivalents exist thereto, such equivalents are incorporated herein as if specifically set forth.

I claim:

1. A process for preparing water dispersible granules comprising a biologically active substance that has a low melting point, the process comprising milling the active substance with a first portion of a finely divided filler to give a finely divided mixture and then blending a second portion of a finely divided filler and a surfactant with the finely divided mixture, wetting the blend with water and then granulating the blend.

2. A process as defined in claim 1 wherein the active substance has a melting point less than 100° C. and a water solubility less than 100 mg/liter at 25° C.

3. A process as defined in claims 1 or 2 wherein the granules comprise 5–75% w/w biologically active substance, 25–90% ww of a finely divided filler and 5–15% w/w of a surfactant component and wherein during the milling stage 20–80% of the filler component is present.

4. A process as defined in claim 1 wherein the concentration of biologically active substance in a premix is at least 1.5 times that of the concentration of the biologically active substance in the final granule.

5. A process as defined in claim 1 wherein the mixture after the milling stage has a particle size less than 50 microns.

6. A process as defined in claim 1 wherein a relatively low pressure extruder is used to extrude the wetted blend as a low compact extrudate than can be broken down by a gentle rolling or tumbling action to form rounded granules which can be subsequently dried.

7. Water dispersible granules prepared by a process as defined in claims 1 or 2.

8. A process according to claim 5 wherein the particle size is less than 10 microns.

* * * * *